United States Patent [19]

Serban et al.

[11] 4,309,211
[45] Jan. 5, 1982

[54] HERBICIDAL 1,2,4-BENZOTRIAZINES

[75] Inventors: Alexander Serban, Doncaster; Graeme J. Farquharson, Reservoir; Graham J. Bird, North Melbourne; Jack Lydiate, Viewbank, all of Australia

[73] Assignee: ICI Australia Limited, Melbourne, Australia

[21] Appl. No.: 178,012

[22] Filed: Aug. 13, 1980

[30] Foreign Application Priority Data

Aug. 31, 1979 [AU] Australia ............................... PE0298

[51] Int. Cl.$^3$ ..................... C07D 253/08; A01N 43/64
[52] U.S. Cl. ......................................... 71/93; 544/183; 260/243.3
[58] Field of Search ............................ 544/183; 71/93; 260/243.3

[56] References Cited

U.S. PATENT DOCUMENTS 4,130,413 12/1978 Handte et al. ........................... 71/90

Primary Examiner—John M. Ford
Attorney, Agent, or Firm—Cushman, Darby & Cushman

[57] ABSTRACT

The invention concerns novel compounds of the formula I

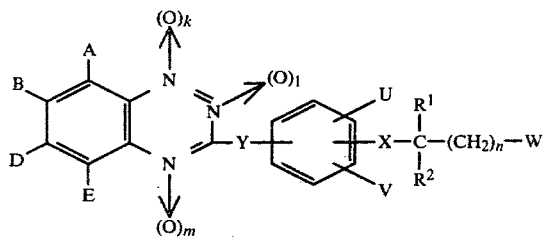

The compounds are herbicides and in further embodiments the invention provides processes for the preparation of compounds of formula I, intermediates useful in the preparation of compounds of formula I, herbicidal compositions containing as active ingredient a compound of formula I, and processes for severely damaging or killing unwanted plants by applying to the plants or to the growth medium of the plants an effective amount of a compound of formula I.

13 Claims, No Drawings

HERBICIDAL 1,2,4-BENZOTRIAZINES

This invention relates to organic compounds having biological activity and in particular to organic compounds having herbicidal properties, to processes for the preparation of such compounds, to intermediates useful in the preparation of such compounds and to herbicidal compositions and processes utilizing such compounds.

We have now found a new class of benzotriazines which exhibit biological activity, and in particular herbicidal activity.

Accordingly the invention provides a compound of formula I:

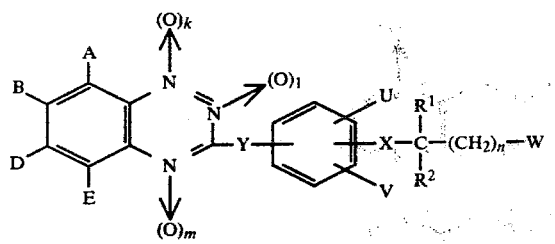

or a salt thereof wherein:

A, B, D, E, U and V are independently chosen from the group consisting of hydrogen, halogen, nitro, cyano, thiocyano, amino, $C_1$ to $C_6$ alkylamino, di($C_1$ to $C_6$ alkyl)amino, $C_1$ to $C_6$ alkyl, $C_1$ to $C_6$ haloalkyl, $C_2$ to $C_6$ alkenyl, $C_3$ to $C_7$ cycloalkyl, $C_1$ to $C_6$ alkoxy, $C_1$ to $C_6$ haloalkoxy, $C_1$ to $C_6$ alkylthio, $C_1$ to $C_6$ alkylsulfinyl, $C_1$ to $C_6$ alkylsulfonyl, $C_1$ to $C_6$ haloalkylsulfinyl, $C_1$ to $C_6$ haloalkylsulfonyl, sulfo, $C_1$ to $C_6$ alkoxysulfonyl, sulfamoyl, N-($C_1$ to $C_6$ alkyl)sulfamoyl, N,N-di($C_1$ to $C_6$ alkyl)sulfamoyl, carboxy, ($C_1$ to $C_6$ alkoxy)carbonyl, carbamoyl, N-($C_1$ to $C_6$ alkyl)carbamoyl, N,N-di($C_1$ to $C_6$ alkyl)carbamoyl, phenyl, phenoxy, phenylthio, and the groups substituted phenyl, substituted phenoxy and substituted phenylthio wherein in each group the phenyl ring is substituted with from 1 to 3 substituents chosen from the group consisting of halogen, $C_1$ to $C_6$ alkyl, $C_1$ to $C_6$ haloalkyl, $C_1$ to $C_6$ alkoxy, nitro and cyano;

$R^1$ is chosen from the group consisting of hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl and $C_2$ to $C_6$ alkoxycarbonyl, $R^2$ is chosen from the group consisting of hydrogen, $C_1$ to $C_6$ alkyl, $C_2$ to $C_6$ alkenyl, $C_2$ to $C_6$ alkoxyalkyl and $C_1$ to $C_6$ haloalkyl, or $R^1$ and $R^2$ together may form a methylene, ethylidene, propylidene or isopropylidene group;

W is chosen from the group consisting of cyano, thiocarbamoyl,

and $CH_2Z$ wherein: G is chosen from the group consisting of hydroxy, mercapto, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, $C_3$ to $C_7$ cycloalkoxy, $C_3$ to $C_7$ cycloalkoxy substituted with 1 or 2 $C_1$ to $C_4$ alkyl groups, phenoxy, phenylthio, benzyloxy, benzylthio, the group $C_1$ to $C_{10}$ alkoxy substituted with a substituent chosen from the group consisting of $C_1$ to $C_6$ alkoxy, amino, ammonio, cyano, N-($C_1$ to $C_6$ alkyl)amino, N,N-di($C_1$ to $C_6$ alkyl)amino and N,N,N-tri($C_1$ to $C_6$ alkyl)ammonio, the groups phenoxy, phenylthio, benzyloxy and benzylthio wherein in each group the phenyl ring is substituted with from 1 to 3 substituents chosen from the group consisting of halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group $-NHSO_2R^3$ wherein $R^3$ is chosen from $C_1$ to $C_{10}$ alkyl and $C_1$ to $C_6$ haloalkyl, the group $-NR^4R_5$ wherein $R^4$ and $R^5$ are independently chosen from the group consisting of hydrogen, $C_1$ to $C_6$ alkyl, phenyl and benzyl or $R^4$ and $R^5$ together form a heterocyclic ring, and the group $-O-N=R^6$ wherein $R^6$ is a $C_1$ to $C_{10}$ alkylidene group;

Z is chosen from the group consisting of halogen, hydroxy, mercapto, $C_1$ to $C_{10}$ alkoxy, $C_1$ to $C_{10}$ haloalkoxy, $C_1$ to $C_{10}$ alkylthio and the group $-NR^4R^5$ wherein $R^4$ and $R^5$ are as hereinbefore defined;

X and Y are independently chosen from oxygen and sulfur;

k, l and m are independently chosen from 0 and 1 provided that k+l+m is 0, 1 or 2; and n is 0, 1 or 2.

The compounds of formula I wherein $R^1$ and $R^2$ are not the same are optically active and the present invention also includes the individual stereo isomers of such compounds, and mixtures of those stereo isomers in addition to the racemic mixture of stereo isomers.

Suitable A, B, D, E, U and V include hydrogen, halogen, nitro, cyano, thiocyano, amino optionally substituted with one or two $C_1$ to $C_6$ alkyl groups, $C_1$ to $C_6$ alkyl optionally substituted with one or more halogen atoms, $C_2$ to $C_6$ alkenyl, $C_3$ to $C_7$ cycloalkyl, $C_1$ to $C_6$ alkoxy, $C_1$ to $C_6$ alkylthio, $C_1$ to $C_6$ alkylsulfinyl, $C_1$ to $C_6$ alkylsulfonyl, carbalkoxy wherein alkoxy is a $C_1$ to $C_6$ alkoxy group, and the groups phenyl, phenoxy or phenylthio wherein in each the phenyl ring is optionally substituted with from one to three substituents chosen from halogen, $C_1$ to $C_6$ haloalkyl, $C_1$ to $C_6$ alkyl, $C_1$ to $C_6$ alkoxy, nitro and cyano.

Suitable $R^1$ include hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl and $C_2$ to $C_6$ alkoxycarbonyl. Suitable $R^2$ include hydrogen, $C_1$ to $C_6$ alkyl, $C_2$ to $C_6$ alkenyl, $C_2$ to $C_6$ alkoxyalkyl and $C_1$ to $C_6$ haloalkyl, or $R^1$ and $R^2$ together may form a methylene, ethylidene, propylidene or isopropylidene group.

Suitable W include cyano, thiocarbamoyl,

and $CH_2Z$ wherein: G is chosen from the group consisting of hydroxy, mercapto, $C_1$ to $C_{10}$ alkoxy optionally substituted with halogen, hydroxy or $C_1$ to $C_6$ alkoxy, $C_1$ to $C_{10}$ alkylthio, $C_2$ to $C_{10}$ alkenyloxy, $C_2$ to $C_{10}$ alkynyloxy, $C_2$ to $C_{10}$ alkenylthio, $C_3$ to $C_7$ cycloalkoxy optionally substituted with one or two $C_1$ to $C_4$ alkyl groups, the groups phenoxy, phenylthio, benzyloxy and benzylthio each optionally substituted in the phenyl ring with one or two substituents chosen from halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group $-NHSO_2R^3$ wherein $R^3$ is chosen from $C_1$ to $C_{10}$ alkyl and $C_1$ to $C_6$ haloalkyl, and the group —NR$^4$R$^5$ wherein R$^4$ and R$^{15}$ are independently chosen from the group consisting of hydrogen, C$_1$ to C$_6$ alkyl optionally substituted with halogen or hydroxy, phenyl and benzyl, or R$^4$ and R$^5$ togther form a heterocyclic ring; and Z is chosen from halogen, hydroxy, mercapto, C$_1$ to C$_{10}$ alkoxy optionally substituted with halogen, C$_1$ to C$_{10}$ alkylthio and the group NR$^4$R$^5$ wherein R$^4$ and R$^5$ are as hereinbefore defined.

Suitable k, l and m include 0 or 1 wherein k+l+m is 0 or 1.

Preferred A, B, D and E include hydrogen, halogen, nitro, cyano, amino, C$_1$ to C$_6$ alkylamino, di(C$_1$ to C$_6$ alkyl)amino, C$_1$ to C$_6$ alkyl, C$_1$ to C$_6$ haloalkyl, C$_2$ to C$_6$ alkenyl, C$_1$ to C$_6$ alkoxy, C$_1$ to C$_6$ haloalkoxy, C$_1$ to C$_6$ alkylthio, carboxy and (C$_1$ to C$_6$ alkoxy)carbonyl.

Preferred U and V include hydrogen, halogen, nitro, cyano, C$_1$ to C$_6$ alkyl and C$_1$ to C$_6$ haloalkyl.

Preferred R$^1$ include hydrogen, C$_1$ to C$_6$ alkyl, C$_2$ to C$_6$ alkoxyalkyl and (C$_1$ to C$_6$ alkoxy)carbonyl.

Preferred R$^2$ include hydrogen and C$_1$ to C$_6$ alkyl.

Preferred W include the groups (a)

$$-\overset{\overset{O}{\|}}{C}-G$$

wherein G is chosen from the group consisting of hydroxy, C$_1$ to C$_{10}$ alkoxy, C$_1$ to C$_{10}$ haloalkoxy, C$_2$ to C$_{10}$ alkenyloxy, C$_2$ to C$_{10}$ alkynyloxy, C$_1$ to C$_{10}$ alkylthio, C$_2$ to C$_{10}$ alkenylthio, C$_2$ to C$_{10}$ alkynylthio, phenoxy, benzyloxy, cyclohexyloxy, the group C$_1$ to C$_{10}$ alkoxy substituted with a substituent chosen from the group consisting of C$_1$ to C$_6$ alkoxy, amino, N-(C$_1$ to C$_6$ alkyl)amino, N,N-di(C$_1$ to C$_6$ alkyl)amino and N,N,N-tri(C$_1$ to C$_6$ alkyl)ammonio, the group NR$^4$R$^5$ wherein R$^4$ and R$^5$ are independently chosen from hydrogen, C$_1$ to C$_6$ alkyl, C$_1$ to C$_6$ hydroxyalkyl, C$_1$ to C$_6$ haloalkyl, and phenyl, the group OM wherein M is an alkali metal ion, alkaline earth metal ion or an ammonium ion HN$^\oplus$R$^7$R$^8$R$^9$ wherein R$^7$, R$^8$ and R$^9$ are independently chosen from the group consisting of hydrogen, C$_1$ to C$_6$ alkyl, C$_1$ to C$_6$ hydroxyalkyl, phenyl and benzyl, the group —NHSO$_2$R$^3$ wherein R$^3$ is C$_1$ to C$_6$ alkyl, and the group —O—N=R$^6$ wherein R$^6$ is a C$_1$ to C$_{10}$ alkylidene group; and (b) the group —CH$_2$Z wherein Z is chosen from the group consisting of halogen, hydroxy, mercapto, C$_1$ to C$_{10}$ alkoxy, and the group —NR$^4$R$^5$ wherein R$^4$ and R$^5$ are independently chosen from the group consisting of hydrogen, C$_1$ to C$_6$ alkyl, C$_1$ to C$_6$ hydroxyalkyl, C$_1$ to C$_6$ haloalkyl and phenyl.

Preferably X and Y are both oxygen.

Preferred m is 0 and preferred k and l are independently 0 and 1 provided that k+l is 0 or 1.

Preferred n is 0 or 2.

More preferably:

A, B, D and E are independently chosen from hydrogen, halogen, C$_1$ to C$_6$ alkyl and C$_1$ to C$_6$ haloalkyl;

U and V are independently chosen from hydrogen and halogen;

R$^1$ and R$^2$ are independently chosen from hydrogen and C$_1$ to C$_6$ alkyl;

W is the group $$-\overset{\overset{O}{\|}}{C}-G$$

wherein G is chosen from hydroxy, C$_1$ to C$_{10}$ alkoxy, C$_2$ to C$_{10}$ alkenyloxy, C$_2$ to C$_{10}$ alkynyloxy, C$_3$ to C$_7$ cycloalkoxy and the group OM wherein M is an alkali metal ion or an alkaline earth metal ion;

X and Y are both oxygen;

k is chosen from 0 and 1; and l, m and n are each 0.

Examples of the compounds embraced by the invention include:

-continued

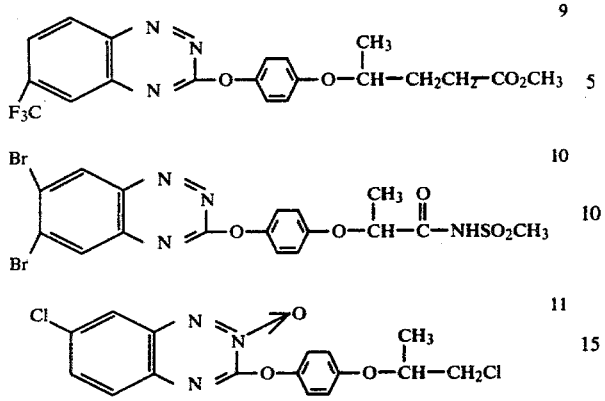

Preferred compounds of formula I are those compounds in which the phenyl ring is 1,4-substituted, that is compounds of formula II

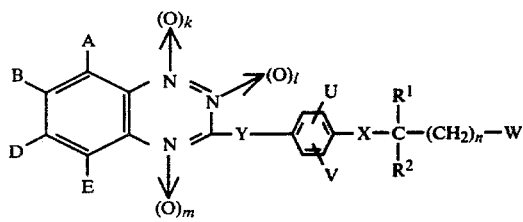

Specific examples of compounds of the invention include those compounds detailed in Table 1 below.

TABLE 1

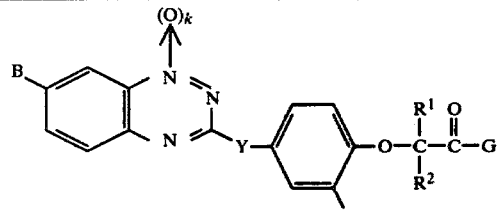

| Compound No | Substituents | | | | | | |
|---|---|---|---|---|---|---|---|
| | B | k | Y | U | $R^1$ | $R^2$ | G |
| 1 | Cl | 1 | O | H | $CH_3$ | H | $CH_3O$ |
| 2 | Cl | 0 | O | H | $CH_3$ | H | $CH_3O$ |
| 12 | H | 1 | O | H | $CH_3$ | H | $C_2H_5O$ |
| 13 | Br | 1 | O | H | $CH_3$ | H | $C_2H_5O$ |
| 14 | F | 1 | O | H | $CH_3$ | H | $C_2H_5O$ |
| 15 | Br | 0 | O | H | $CH_3$ | H | $C_2H_5O$ |
| 16 | Cl | 0 | O | H | $CH_3$ | H | $C_2H_5O$ |
| 17 | Cl | 0 | O | H | $CH_3$ | H | a |
| 18 | Cl | 0 | O | H | $CH_3$ | H | $n\text{-}C_4H_9O$ |
| 19 | Cl | 0 | O | H | $CH_3$ | H | $n\text{-}C_3H_7O$ |
| 20 | Cl | 0 | S | H | $CH_3$ | H | $C_2H_5O$ |
| 21 | $CF_3$ | 1 | O | H | $CH_3$ | H | $C_2H_5O$ |
| 22 | $C_2H_5$ | 1 | O | H | $CH_3$ | H | $C_2H_5O$ |
| 23 | Cl | 1 | O | H | H | H | $C_2H_5O$ |
| 24 | F | 1 | O | F | $CH_3$ | H | $C_2H_5O$ |
| 25 | F | 1 | O | H | $CH_3$ | $CH_3$ | $C_2H_5O$ |
| 26 | F | 0 | O | H | $CH_3$ | H | $C_2H_5O$ |
| 27 | H | 0 | O | H | $CH_3$ | H | $C_2H_5O$ |
| 28 | $CH_3$ | 0 | O | H | $CH_3$ | H | $C_2H_5O$ |
| 29 | $CH_3$ | 1 | O | H | $CH_3$ | H | $C_2H_5O$ |

Footnote:
a - cyclohexyloxy

The compounds of the invention may be prepared by a variety of methods and in a further aspect the invention provides methods for the preparation of the compounds of formula I.

Compounds of formula Ia

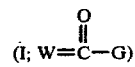

(I; W=C—G)

wherein G is not hydroxy may be prepared from the acid of formula Ib (I; W=—$CO_2H$) by, for example, neutralisation of the acid with a base to give an acid salt, esterification of the acid with an alcohol, thiol, phenol or thiophenol to give an acid ester, or reaction of the acid (or acid halide derivative thereof) with an amine to give an amide (SCHEME A). Processes known in the art for the preparation of acid salts, acid esters, acid halides and acid amides may be adapted, without undue experimentation, to prepare compounds of the invention of formula Ia from compounds of the invention of formula Ib.

SCHEME A

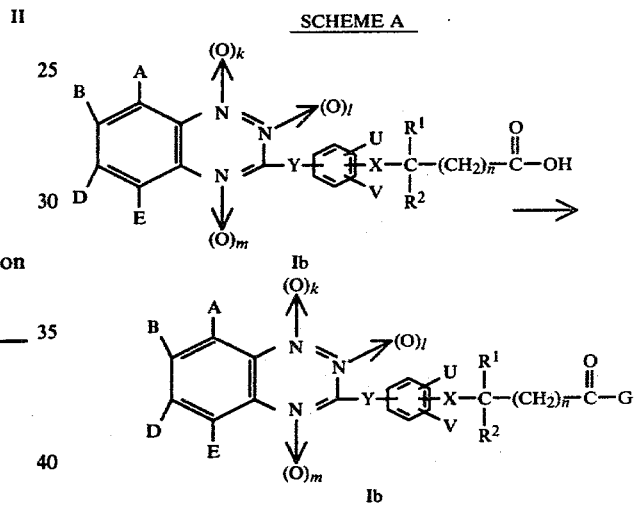

Nitriles of the invention of formula Ic (I; W=—C≡N) may be prepared, for example, from the acid amide of formula Id (I; W=—$CONH_2$) (SCHEME B).

SCHEME B

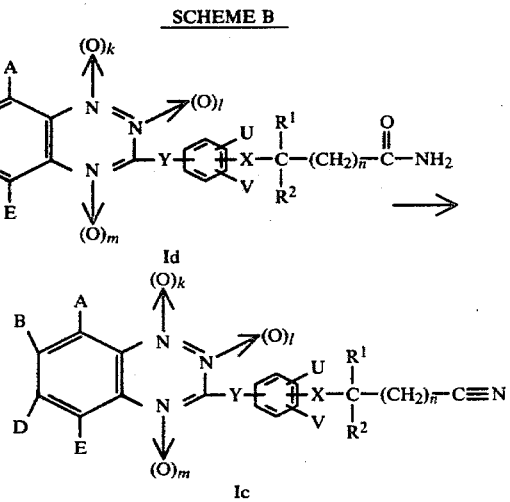

Alcohols of the invention of formula Ie (I; W=—CH₂OH) may be prepared from the acid or acid esters of formula If (I;

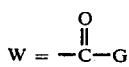

wherein G=OH or O-alkyl) by reduction (SCHEME C). Processes known in the art for the reduction of acids or acid esters to alcohols, for example lithium aluminium hydride reduction, may be adapted, without undue experimentation, to prepare alcohols of the invention of formula Ie from esters of the invention of formula If.

SCHEME C

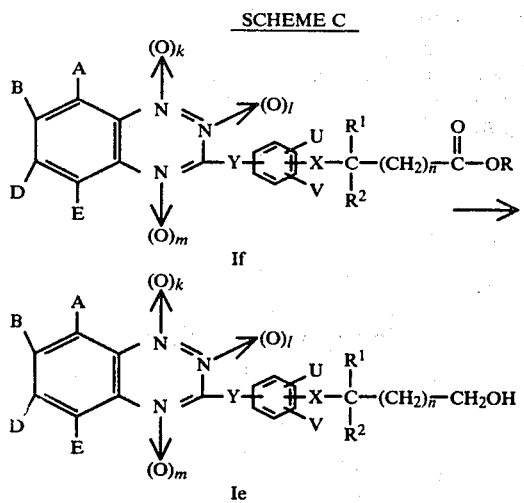

Alkyl halides of the invention of formula Ig (I; W=—CH₂-halogen) may be prepared from alcohols of formula Ie (I; W=—CH₂OH) by halogenation. Processes known in the art for the conversion of alcohols to alkyl halides, for example halogenation with reagents such as thionyl chloride, may be adapted, without undue experimentation, to prepare alkyl halides of the invention of formula Ig from alcohols of the invention of formula Ie.

Ethers of the invention of formula Ih (I; W=—CH₂OR) may be prepared from alcohols of formula Ie (I; W=—CH₂OH) by alkylation. Processes known in the art for the conversion of alcohols to ethers, for example by reaction with alkyl halides using the Williamson ether synthesis, may be adapted, without undue experimentation, to prepare ethers of the invention of formula Ih from alcohols of the invention of formula Ie.

Ethers (thioethers) of the invention of formula Ih (Ii) [I; W=—CH₂OR(—CH₂SR)] may be prepared from alkyl halides of formula Ig (I; W=CH₂-halogen) by alkoxylation (thioalkoxylation). Processes known in the art for the conversion of alkyl halides to ethers (thioethers), for example by reaction with alcohols (thiols) using the Williamson ether synthesis, may be adapted, without undue experimentation, to prepare ethers (thioethers) of the invention of formula Ih (Ii) from alkyl halides of the invention of formula Ig.

Amines of the invention of formula Ij (I; W=—CH₂NR⁴R⁵) may be prepared from the alkyl halides of formula Ig (I; W=—CH₂-halogen) by amination or from the amides of formula Ik

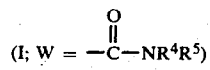

by reduction. Processes known in the art for the conversion of alkyl halides to amines, for example by reaction with amines, and for the conversion of amides to amines, for example by reduction with agents such as lithium aluminium hydride, may be adapted without undue experimentation, to prepare amines of the invention of formula Ij from alkyl halides of the invention of formula Ig and from amides of the invention of formula Ik respectively.

N-oxides of the invention of formula I wherein k and/or l and/or m is 1 may be prepared from compounds of the invention of formula I wherein k and/or l and/or m is 0 by oxidation. Processes known in the art for the conversion of benzotriazines to benzotriazine N-oxides, for example oxidations using persulfates, peroxides, peracids or peresters, may be adapted without undue experimentation, to prepare N-oxides of the invention.

Compounds of formula I wherein A, B, D, E, U, V, Y, X, R¹, R², W, k, l, m and n are as hereinbefore defined may be prepared by the condensation of a phenol or thiophenol of formula IX with a compound of formula X wherein hal is chlorine, bromine or iodine, preferably in the presence of an alkaline material; according to SCHEME D.

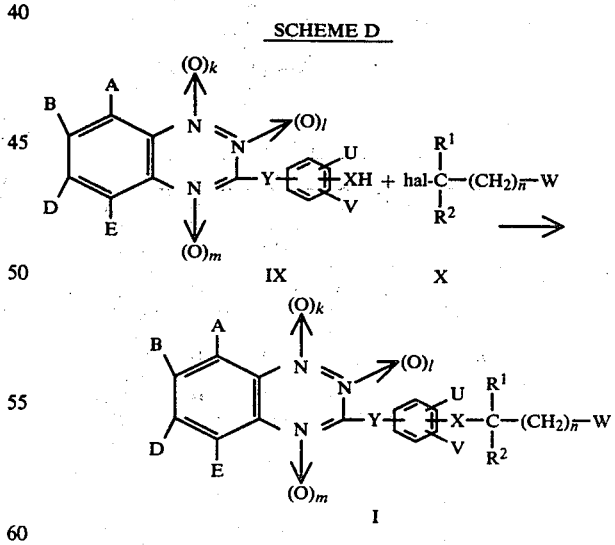

Compounds of formula I may also be prepared by:
(a) the condensation of the appropriate benzotriazine derivative of formula V, wherein L is a leaving group (for example, alkylsulfonyl, chlorine, bromine or iodine) with the appropriate phenol or thiophenol of formula VI according to SCHEME E.

SCHEME E

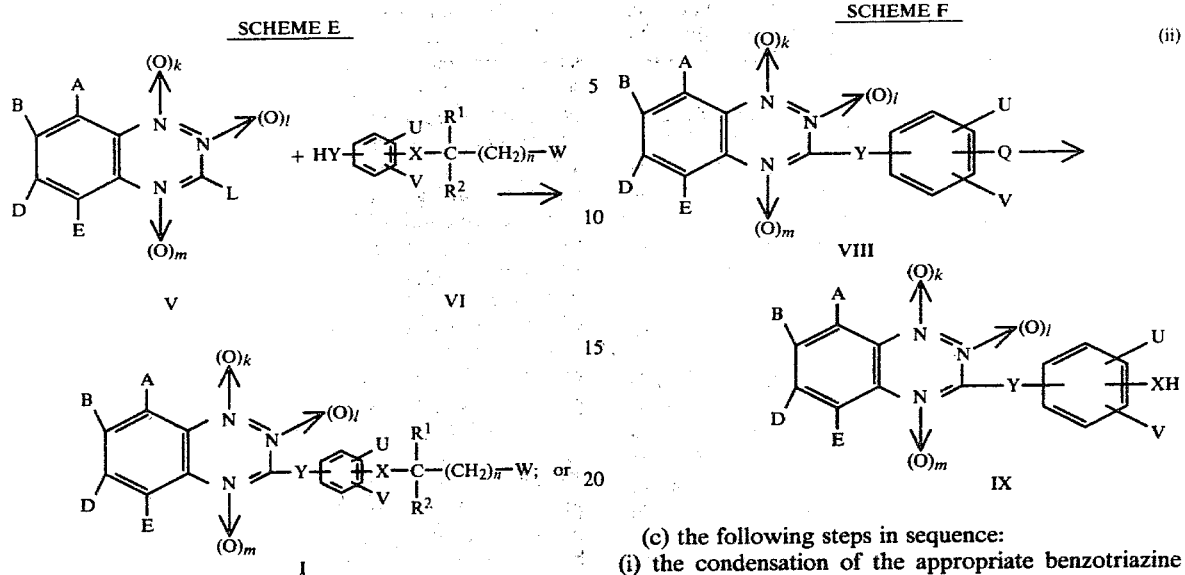

(b) the following steps in sequence:
(i) the condensation of the appropriate benzotriazine derivative of formula V, wherein L is a leaving group (for example, alkylsulfonyl, chlorine, bromine or iodine) with the appropriate compound of formula VII, wherein Q is hydroxy, mercapto, $C_1$ to $C_6$ alkoxy or $C_1$ to $C_6$ alkylthio to give a compound of formula VIII wherein Q is hydroxy, mercapto, $C_1$ to $C_6$ alkoxy or $C_1$ to $C_6$ alkylthio;

(ii) the dealkylation of the compound of formula VIII prepared in step (i) above wherein Q is $C_1$ to $C_6$ alkoxy or $C_1$ to $C_6$ alkylthio to give a compound of formula IX; and (iii) the condensation of the product of formula IX obtained in step (i) or step (ii) above with a compound of formula X according to the process described for SCHEME D above (Steps (i) and (ii) are shown in SCHEME F); or

SCHEME F

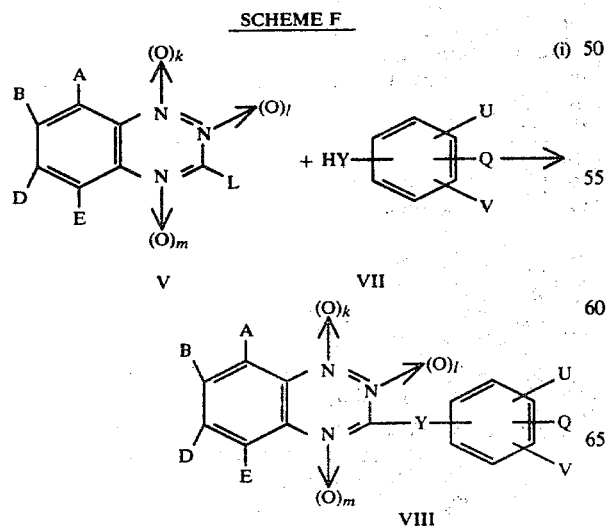

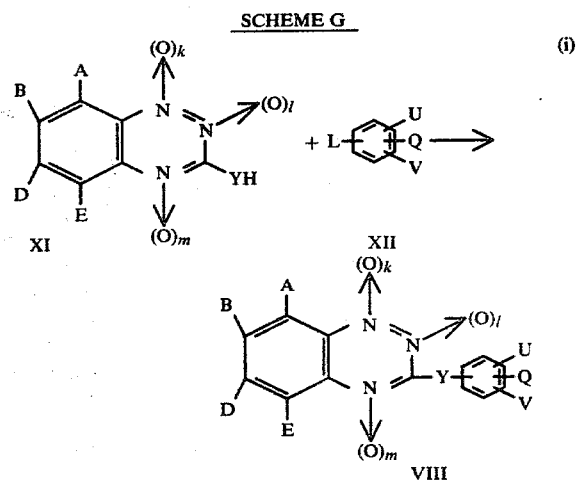

(c) the following steps in sequence:
(i) the condensation of the appropriate benzotriazine derivative of formula XI with the appropriate benzene derivative of formula XII wherein L is a leaving group (for example, alkylsulfonyl, chlorine, bromine or iodine) and Q is hydroxy, mercapto, $C_1$ to $C_6$ alkoxy or $C_1$ to $C_6$ alkylthio, to give a compound of formula VIII wherein Q is as hereinbefore defined;

(ii) the dealkylation of the compound of formula VIII prepared in step (i) above wherein Q is $C_1$ to $C_6$ alkoxy or $C_1$ to $C_6$ alkylthio, to give a compound of formula IX according to the process described for SCHEME F step (ii) above; and (iii) the condensation of the product of formula IX obtained in step (i) or step (ii) above with a compound of formula X according to the process described for SCHEME D above (step (i) is shown in SCHEME G).

SCHEME G

The condensation reactions illustrated in SCHEMES D to G and outlined above are preferably carried out in the presence of an alkaline material and preferably in the presence of a solvent. Suitable alkaline materials include alkali metal and alkaline earth metal hydroxides and carbonates such as sodium hydroxide, potassium hydroxide, sodium carbonate and potassium carbonate. Suitable solvents include ketones such as, for example, acetone, methyl ethyl ketone and methyl isobutyl ketone, and dipolar aprotic solvents such as, for example, dimethylformamide, dimethylacetamide, dimethylsulfoxide, N-methylpyrrolidone, hexamethylphosphoramide and sulfolan.

The reaction conditions required to effect the condensation reactions illustrated in SCHEMES D, E, F, and G and outlined above vary according to the nature of the reactants and the solvent used. In general the reaction is facilitated by the application of heat and usually a reaction temperature in the range of 40° to 150° C. and reaction time of between 0.5 and 20 hours is satisfactory. However, higher or lower reaction temperatures and/or shorter or longer reaction times may be used if desired.

The dealkylation reactions illustrated in SCHEMES F and G and outlined in paragraphs (b) (ii) and (c) (ii) above may be effected using a variety of reagents known in the art. For example, aryl-alkyl ethers may be cleaved using reagents such as pyridine hydrochloride, hydriodic acid, hydrobromic acid, sodium thioethoxide in dimethylformamide, acetyl p-toluenesulphonate, sodium or potassium iodide in formic or acetic acid, lithium iodide in 2,4,6-collidine and boron tribromide. Reaction times and reaction conditions vary widely depending on the dealkylation agent used and the ether to be cleaved. The reaction conditions generally employed when using the above "ether-cleavage" reagents are known to those skilled in the art and may be adapted without undue experimentation to effect the "ether-cleavage" reactions illustrated in SCHEMES F and G and outlined in paragraph (b) (ii) and (c) (ii) above.

The compounds of formula V

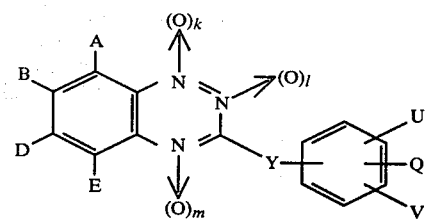

VIII which are useful intermediates in the preparation of compounds of formula I, are also believed to be novel compounds. Therefore, in a further embodiment the invention provides compounds of formula VIII wherein A, B, D, E, k, l, m, Y, U, V and Q are as hereinbefore defined.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to kill or severely damage monocotyledonous weeds in a monocotyledonous cereal crop.

Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (preemergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

Compositions according to the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, eg kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (eg cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl- and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octyl-cresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may be sufficient to protect a crop. Accordingly in yet a still further embodiment the invention provides a herbicidal composition comprising a mixture of at least one herbicidal compound of formula I are hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichloroprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (commond name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)-carbamate (common name phenmedipham) and 3-[(ethoxycarbonyl)amino]phenyl phenylcarbamate (common name desmedipham);

H. 2-phenylpyridazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(isopropylamino)-6-methylthio-1,3,5-triazine (common name aziprotryne);

K. 1-alkoxy-1-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropylthiocarbamate (common name verolate);

M. 1,2,4-triazin-5-one herbicides such as 4-amino-4,5-dihydro-3-methyl-6-phenyl-1,2,4-triazine-5-one (common name metamitron) and 4-amino-6-tertbutyl-4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben).

O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil).

Q. haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid, 2-chloro-4-trifluoromethylphenyl 3-ethoxy-4-nitrophenyl ether and the compounds disclosed in European Pat. publication No. 3,416; and S. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

T. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat), U. organoarsenical herbicides such as monosodium methanearsonate (common name MSMA); and V. amino acid herbicides such as N-(phosphonomethyl)glycine (common name glyphosate) and its salts and esters.

The invention is now illustrated by, but in no way limited to, the following Examples.

EXAMPLE 1

Methyl 2-{4-[(7-chloro-1-oxide-1,2,4-benzotriazin-3-yl)oxy]phenoxy}propionate (1)

A mixture of 3,7-dichloro-1,2,4-benzotriazine 1-oxide* (1.5 g), methyl 2-(4-hydroxyphenoxy)propionate (1.4 g), anhydrous potassium carbonate (1.2 g) and acetonitrile (30 ml) was heated under reflux for a period of 18 hours. The solvent was removed by distillation under reduced pressure and the residue was partitioned between water and chloroform. The chloroform layer was dried and the solvent was removed by distillation under reduced pressure to give a dark oil (2.5 g). The oil was chromatographed over silica gel (80 g) with chloroform elution to give methyl 2-{4-[(7-chloro-1-oxide-1,2,4-benzotriazin-3-yl)oxy]phenoxy}propionate as a yellow solid. Proton magnetic resonance spectrum (CDCl$_3$; in ppm) 6.7–7.0 (7H, m, aromatic proton); 4.6 (1H, q, —O—C$\underline{H}$—CH$_3$); 3.7(3H, s, —CO$_2$C$\underline{H}_3$); 1.5 (3H, d, O—CH—C$\underline{H}_3$). Mass spectrometry: Found M+ (molecular ion) at m/e 375; C$_{17}$H$_{14}$ClN$_3$O$_5$ requires 375.

*Prepared according to the process of J. Jiu and G. P. Mueller, J. Org. Chem., 24, 813–818 (1959). See also F. J. Wolf, R. M. Wilson, K. P. Fister and M. Tishler, J. Amer. Chem. Soc., 76, 4611–4613 (1954). For further information on the preparation of the 1,2,4-benzotriazines used as starting materials see the references cited in "Chemistry of 1,2,3-triazines and 1,2,4-triazines, tetrazines and pentazines", H Neunhoeffer and P F Wiley, pp 666–1043, John Wiley and Sons, New York, 1978 (One of the series of monographs entitled "The Chemistry of Heterocyclic Compounds", Editors A Weissberger and E C Taylor).

EXAMPLE 2

Ethyl 2-{4-[(7-bromo-1,2,4-benzotriazin-3-yl)oxy]phenoxy}propionate (15)

A mixture of 7-bromo-3-chloro-1,2,4-benzotriazine (1.93 g), ethyl 2-(4-hydroxyphenoxy)propionate (1.69 g), anhydrous potassium carbonate (1.20 g) and methyl ethyl ketone (50 ml) was heated under reflux overnight. The solvent was removed by distillation under reduced pressure and the residue was partitioned between water and dichloromethane. The organic layer was separated, dried (over anhydrous magnesium sulfate) and the solvent was removed by distillation under reduced pressure to give an oil. The crude product was purified by chromatography over silica gel (eluent dichloromethane) and the product was recrystallised from aqueous ethanol to give the title compound (1.16 g) as yellow crystals, mp 104° C.

The assigned structure was confirmed by proton magnetic resonance spectroscopy and mass spectrometry.

EXAMPLE 3

The compounds no 2, 12, 13, 14, 16, 17, 18, 19, 21, 22, 26, 27, 28 and 29 were prepared from the appropriate benzotriazine and the appropriate alkyl 2-(4-hydroxyphenoxy)propionate; compound no 23 was prepared from 3,7-dichloro-1,2,4-benzotriazine-1-oxide and ethyl 2-(4-hydroxyphenoxy)acetate; and compound no 24 was prepared from 3-chloro-7-fluoro-1,2,4-benzotriazine-1-oxide and ethyl 2-(2-fluoro-4-hydroxyphenoxy)propionate; all following essentially the same procedure as that described in Example 1 or Example 2.

The structure assigned to each compound was confirmed by proton magnetic resonance spectroscopy and mass spectrometry and appropriate physical data is recorded in Example 6, Table 2.

EXAMPLE 4

Ethyl 2-{4-[(7-chloro-1,2,4-benzotriazin-3-yl)thio]phenoxy}propionate (20)

(a) A mixture of 3,7-dichloro-1,2,4-benzotriazine (1.50 g) 4-mercaptophenol (0.95 g), sodium (0.17 g) and ethanol (50 ml) was stirred at room temperature for a period of 30 minutes. The solvent was removed by distillation under reduced pressure and the residue was partitioned between water and ethyl acetate. The organic phase was dried (over anhydrous magnesium sulfate) and the solvent was removed by distillation under reduced pressure to give 4-[(7-chloro-1,2,4-benzotriazin-3-yl)thio]phenol (1.83 g) as orange crystals, mp 238° C.

(b) A mixture of 4-[(7-chloro-1,2,4-benzotriazin-3-yl)thio]phenol (1.83 g), ethyl 2-bromopropionate (1.37 g), anhydrous potassium carbonate (0.96 g) and methyl ethyl ketone (50 ml) was heated under reflux for a period of 3 hours. The solvent was removed by distillation under reduced pressure and the residue was partitioned between water and dichloromethane. The organic phase was separated, dried (over anhydrous magnesium sulfate) and the solvent was removed by distillation under reduced pressure to give a solid. The crude product was purified by chromatography over silica gel (eluent dichloromethane) to give the title compound (1.95 g) as a crystalline solid, mp 86°–88° C.

The assigned structure was confirmed by proton magnetic resonance spectroscopy and mass spectrometry.

EXAMPLE 5

Ethyl 2-{4-[(7-fluoro-1-oxide-1,2,4-benzotriazin-3-yl)oxy]-phenoxy}-2-methylpropionate (25)

A mixture of 3-chloro-7-fluoro-1-oxide-1,2,4-benzotriazine (0.22 g), ethyl 2-(4-hydroxyphenoxy)-2-methylpropionate (0.25 g), anhydrous potassium carbonate (0.17 g) and dimethylformamide (20 ml) was heated at a temperature of 100° C. for a period of 24 hours. The cooled mixture was poured into dichloromethane and the mixture was washed with water. The organic phase was separated, dried (over anhydrous magnesium sulfate) and the solvent was removed by distillation under reduced pressure to give a brown oil. The crude product was purified by chromatography over silica gel (eluent dichloromethane) to give the title compound (0.40 g) as a yellow oil.

The assigned structure was confirmed by proton magnetic resonance spectroscopy and mass spectrometry. Pmr spectrum δ ppm (CDCl$_3$): 1.30,t,3H; 1.60,s,6H; 4.30,q,2H; 7.15,m,4H; 7.6–8.4,m,3H.

EXAMPLE 6

A number of the compounds of the invention detailed in Table 1 are solids and can be identified by melting point. For convenience the melting points are tabulated in Table 2a below.

Some of the compounds of the invention detailed in Table 1 are oils and were characterised by, and can be identified by, their proton magnetic resonance (pmr) spectrum. For convenience the pmr spectroscopic data is recorded in Table 2b below:

TABLE 2a

| Compound No | Melting Point °C. | Compound No | Melting Point °C. |
|---|---|---|---|
| 13 | 126 | 23 | 122 |
| 15 | 104 | 24 | 120 |
| 16 | 93 | 26 | 72 |
| 18 | 48 | 27 | 85 |
| 19 | 86 | 28 | 93 |
| 20 | 86–88 | 29 | 136 |

TABLE 2b

| Compound No | Proton Chemical Shift δ in ppm (CDCl$_3$) |
|---|---|
| 1 | 1.50,d,3H; 3.70,s,3H; 4.60,q,1H; 6.7–7.0,m,7H. |
| 2 | 1.65,d,3H; 3.80,s,3H; 4.85,q,1H; 7.20,m,4H; 7.80,s,2H; 8.60,s,1H. |
| 12 | 1.30,t,3H; 1.65,d,3H; 3.65,s,3H; 4.30,q,2H; 4.85,q,1H; 7.20,m,4H; 7.35,m,1H; 7.65,m,2H; 8.30,d,1H. |
| 14 | 1.30,t,3H; 1.65,d,3H; 4.30,q,2H; 4.80,q,1H; 7.20,m,4H; 7.6–8.3,m,3H. |

TABLE 2b-continued

| Compound No | Proton Chemical Shift δ in ppm (CDCl$_3$) |
|---|---|
| 17 | 1.50,m,13H; 4.90,m,2H; 7.20,m,4H; 7.80,s,2H; 8.60,s,1H. |
| 21 | 1.30,t,3H; 1.65,d,3H; 4.30,q,2H; 4.80,q,1H; 7.15,m,4H; 8.00,m,2H; 8.65,s,1H. |
| 22 | 1.30,m,6H; 1.65,d,3H; 2.85,q,2H; 4.30,q,2H; 4.80,q,1H; 7.20,m,4H; 7.60,s,2H; 8.20,s,1H. |
| 25 | 1.30,t,3H; 1.60,s,6H; 4.30,q,2H; 7.15,m,4H; 7.6–8.4,m,3H. |

EXAMPLE 7

Concentrated formulations of the compounds of the invention were prepared by:

(a) in the case of oils and waxy solids, dissolving the compound in toluene containing 7% v/v "Teric" N13 ("Teric" is a Trade Mark and "Teric" N13, a product of ethoxylation of nonylphenol, is available from ICI Australia Limited) and 3% v/v "Kemmat" SC15B ("Kemmat" is a Trade Mark and "Kemmat" SC15B is a formulation of calcium dodecylbenzene sulfonate); or (b) in the case of crystalline solids, adding 5 parts by weight of the compound and 1 part by weight of "Dyapol" PT ("Dyapol" is a Trade Mark and "Dyapol" PT is an anionic suspending agent) to 94 parts by weight of an aqueous solution containing 0.25% v/v of "Teric" N8 (a product of ethoxylation of nonylphenol) and ball-milling the mixture to produce a stable suspension. The emulsifiable concentrates and suspensions were then diluted with water to give an aqueous composition of the required concentration suitable for use in the evaluation of the pre-emergence and post-emergence herbicidal activity of the compounds of the invention.

EXAMPLE 8

The pre-emergent herbicidal activity of the compounds of the invention formulated as described in Example 7 was assessed by the following procedure.

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glasshouse and the effect of the treatment was visually assessed. The results are presented in Table 3 where the damage to plants is rated on a scale of from 0 to 3 where 0 represents from 0 to 25% damage, 3 represents 75 to 99% kill and 3+ represents 100% kill. A dash (—) means that no experiment was carried out.

The names of the test plants are as follows:

TABLE 3

| Wh | Wheat |
|---|---|
| Ot | Wild Oats |
| Rg | Ryegrass |
| Jm | Japanese millet |
| P | Peas |
| Ip | Ipomea |
| Ms | Mustard |

TABLE 3-continued

| Sf | Sunflower |

PRE-EMERGENCE HERBICIDAL ACTIVITY

| Compound No. | Application Rate kg/ha | Wh | Ot | Rg | Jm | P | Ip | Ms | Sf |
|---|---|---|---|---|---|---|---|---|---|
| 1 | 5 | 2 | 3+ | 2 | 3+ | 0 | 0 | 0 | 0 |
| 1 | 1 | 0 | 0 | 0 | 3 | 0 | 0 | 0 | 0 |
| 1 | 0.5 | 0 | 1 | 0 | 3 | 0 | 0 | 0 | 0 |
| 12 | 10 | 3 | 3 | 3+ | 3+ | 0 | 0 | 0 | 0 |
| 14 | 5 | 3+ | 3+ | 2 | 3+ | 0 | 0 | 0 | 0 |
| 14 | 1 | 0 | 0 | 0 | 3+ | 0 | 0 | 0 | 0 |
| 22 | 5 | 1 | 1 | 3 | 3+ | 0 | 0 | 0 | 0 |
| 22 | 1 | 0 | 0 | 0 | 0 | 0 | 0 | 0 | 0 |

EXAMPLE 9

The post-emergent herbicidal activity of the compounds of the invention formulated as described in Example 7 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glasshouse, lightly watered with an overhead spray to initiate germination and then subirrigated as required for optimum plant growth. After the plants had grown to a height of about 10 to 12.5 cm one box of each of the monocotyledonous plants and the dicotyledonous plants was removed from the glasshouse and sprayed with the required quantity of a composition of the invention. After spraying the boxes were returned to the glasshouse for a further 3 weeks and the effect of treatment was visually assessed by comparison with the untreated controls. The results are presented in Table 4 where the damage to plants is rated on a scale of from 0 to 3 where 0 represents 0 to 25% damage, 3 represents 75 to 99% kill and 3+ represents 100% kill. A dash (—) means that no experiment was carried out.

The names of the test plants are as follows:

TABLE 4

| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

POST-EMERGENCE HERBICIDAL ACTIVITY

| Compound No. | Application Rate kg/ha | Wh | Ot | Rg | Jm | P | Ip | Ms | Sf |
|---|---|---|---|---|---|---|---|---|---|
| 1 | 5 | 3+ | 3+ | 3+ | 3+ | 0 | 0 | 0 | 0 |
| 1 | 1 | 3 | 3+ | 3+ | 3+ | 0 | 0 | 0 | 0 |
| 1 | 0.5 | 2 | 3+ | 0 | 3+ | 0 | 0 | 0 | 0 |
| 12 | 10 | 2 | 2 | 2 | 3+ | 0 | 0 | 0 | 0 |
| 14 | 5 | 3+ | 3+ | 3+ | 3+ | 0 | 0 | 0 | 0 |
| 14 | 1 | 3+ | 3+ | 1 | 3+ | 0 | 0 | 0 | 0 |
| 22 | 5 | 3 | 3 | 3 | 3+ | 0 | 0 | 0 | 0 |
| 22 | 1 | 1 | 0 | 1 | 3+ | 0 | 0 | 0 | 0 |

EXAMPLE 10

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 5 below. Damage to test plants were assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 5 below. A dash (—) means that no experiment was carried out.

The names of the test plants were as follows:

TABLE 5 - PART A

| Sb | Sugar beet |
| Rp | Rape |
| Ct | Cotton |
| Sy | Soy bean |
| Mz | Maize |
| Mw | Winter wheat |
| Rc | Rice |
| Sn | *Senecio vulgaris* |
| Ip | *Ipomea purpurea* |
| Am | *Amaranthus retroflexus* |
| Pi | *Polygonum aviculare* |
| Ca | *Chenopodium album* |
| Po | *Portulaca oleracea* |
| Ga | *Galium aparine* |
| Xa | *Xanthium pensylvanicum* |
| Ab | *Abutilon theophrasti* |
| Cv | *Convolvulus arvensis* |
| Co | *Cassia obtusifolia* |
| Av | *Avena fatua* |
| Dg | *Digitaria sanguinalis* |

TABLE 5 - PART A-continued

| | |
|---|---|
| Pu | *Poa annua* |
| Al | *Alopecurus myosuroides* |
| St | *Setaria viridis* |
| Ec | *Echinochloa crus-galli* |
| Sh | *Sorghum halepense* |
| Ag | *Agropyron repens* |
| Cn | *Cyperus rotundas* |

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 1 | PRE | 2.0 | 0 | 0 | 0 | 0 | 5 | 4 | 5 | 3 | 0 | 3 | 0 | — |
| 1 | PRE | 0.5 | 0 | 0 | 0 | 0 | 4 | 4 | 5 | 0 | 0 | 2 | 0 | — |
| 1 | POST | 2.0 | 0 | 0 | 0 | 0 | 5 | 5 | 4 | 3 | 0 | 2 | 0 | 0 |
| 1 | POST | 0.5 | 0 | 1 | 0 | 0 | 5 | 4 | 4 | 1 | 1 | 1 | 0 | 1 |
| 2 | PRE | 2.0 | 0 | 0 | 0 | — | 4 | 4 | 5 | 0 | 0 | 0 | 0 | 0 |
| 2 | PRE | 1.0 | 0 | 0 | 0 | 0 | 4 | 2 | 5 | 0 | 0 | 0 | 1 | 2 |
| 2 | POST | 2.0 | 1 | 0 | 0 | 2 | 5 | 2 | 2 | 0 | 0 | 0 | 0 | 0 |
| 2 | POST | 1.0 | 1 | 0 | 0 | 2 | 5 | 1 | 1 | 1 | 0 | — | 0 | 0 |
| 12 | PRE | 2.0 | — | — | — | — | 5 | 5 | 5 | — | — | — | — | — |
| 12 | PRE | 0.5 | — | — | — | — | 3 | 2 | 5 | — | — | — | — | — |
| 12 | POST | 2.0 | — | — | — | — | 4 | 4 | 4 | — | — | — | — | — |
| 12 | POST | 0.5 | — | — | — | — | 3 | 3 | 2 | — | — | — | — | — |
| 14 | PRE | 0.2 | 1 | 0 | 0 | 0 | 1 | 4 | 5 | 0 | 0 | — | 0 | 0 |
| 14 | PRE | 0.05 | 1 | 0 | 1 | 0 | 1 | 3 | 5 | 0 | 0 | — | 0 | 0 |
| 14 | POST | 0.2 | 0 | 0 | 0 | 0 | 5 | 1 | 2 | 0 | 0 | 1 | 0 | 0 |
| 14 | POST | 0.05 | 1 | 1 | 0 | 0 | 4 | 1 | 0 | 0 | 0 | 1 | 0 | 1 |
| 22 | PRE | 2.0 | 0 | 0 | 0 | 0 | 4 | 4 | 4 | 0 | 0 | 1 | — | 2 |
| 22 | PRE | 0.5 | 0 | 0 | 0 | 0 | 1 | 2 | 2 | 0 | 0 | 0 | — | 2 |
| 22 | POST | 2.0 | 0 | 0 | 0 | 0 | 2 | 1 | 0 | 0 | 0 | — | — | 0 |
| 22 | POST | 0.5 | 0 | 0 | 0 | 0 | 0 | 0 | 0 | 0 | 0 | — | — | 0 |

TABLE 5 - PART B

| Compound No | APPLICATION Method | Rate (kg/ha) | Po | Xa | Ab | Cv | Av | Dg | Pu | St | Ec | Sh | Ag | Cn |
|---|---|---|---|---|---|---|---|---|---|---|---|---|---|---|
| 1 | PRE | 2.0 | 2 | 0 | 1 | — | 5 | 5 | 5 | 5 | 5 | 5 | 4 | 0 |
| 1 | PRE | 0.5 | 2 | 0 | 0 | — | 4 | 5 | 4 | 5 | 5 | 4 | 1 | 0 |
| 1 | POST | 2.0 | 0 | 2 | 0 | 0 | 5 | 5 | 2 | 4 | 5 | 5 | 4 | 0 |
| 1 | POST | 0.5 | 0 | 0 | 0 | 0 | 5 | 5 | 0 | 4 | 5 | 5 | 4 | 0 |
| 2 | PRE | 2.0 | 0 | 0 | 0 | — | 0 | 4 | 0 | 4 | 3 | 0 | 1 | 0 |
| 2 | PRE | 1.0 | 1 | 0 | 0 | — | 2 | 4 | 0 | 4 | 3 | 2 | 1 | 0 |
| 2 | POST | 2.0 | — | 0 | 0 | 0 | 4 | 4 | 0 | 2 | 5 | 4 | 1 | — |
| 2 | POST | 1.0 | 2 | 0 | 0 | 1 | 4 | 4 | 0 | 4 | 5 | 4 | 0 | 0 |
| 14 | PRE | 0.2 | — | 0 | 2 | — | 4 | 5 | — | 4 | 5 | 4 | 1 | 0 |
| 14 | PRE | 0.05 | — | 0 | 1 | — | 3 | 3 | — | 4 | 3 | 0 | 1 | 0 |
| 14 | POST | 0.2 | — | 0 | 0 | — | 4 | 4 | — | 4 | 5 | 4 | 0 | 0 |
| 14 | POST | 0.05 | — | 0 | 1 | — | 4 | 4 | — | 4 | 4 | 4 | 1 | 0 |

| Compound No | APPLICATION Method | Rate (kg/ha) | Ga | Xa | Ab | Co | Av | Dg | Al | St | Ec | Sh | Ag | Cn |
|---|---|---|---|---|---|---|---|---|---|---|---|---|---|---|
| 12 | PRE | 2.0 | — | — | — | — | 4 | 5 | 5 | 5 | 5 | 4 | 5 | — |
| 12 | PRE | 0.5 | — | — | — | — | 3 | 4 | 5 | 5 | 5 | 4 | 5 | — |
| 12 | POST | 2.0 | — | — | — | — | 4 | 4 | 4 | 4 | 5 | 4 | 3 | — |
| 12 | POST | 0.5 | — | — | — | — | 4 | 1 | 4 | 4 | 4 | 4 | 1 | — |
| 22 | PRE | 2.0 | — | 0 | 0 | 0 | 0 | 4 | 4 | 4 | 5 | 4 | 5 | — |
| 22 | PRE | 0.5 | — | 1 | 0 | 0 | 0 | 1 | 2 | 1 | 4 | 4 | 3 | — |
| 22 | POST | 2.0 | 0 | 0 | 0 | 0 | 2 | 0 | 0 | 1 | 3 | 3 | 2 | — |
| 22 | POST | 0.5 | 0 | 0 | 0 | 0 | 1 | 0 | 0 | 0 | 0 | 0 | 0 | — |

We claim:
1. A compound of formula I

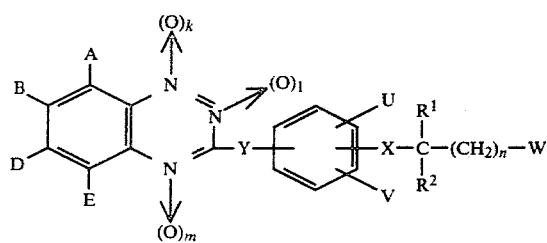

or a salt thereof wherein:

A, B, D, E, U and V are independently chosen from the group consisting of hydrogen, halogen, nitro, cyano, thiocyano, amino, $C_1$ to $C_6$ alkylamino, di($C_1$ to $C_6$ alkyl)amino, $C_1$ to $C_6$ alkyl, $C_1$ to $C_6$ haloalkyl, $C_2$ to $C_6$ alkenyl, $C_3$ to $C_7$ cycloalkyl, $C_1$ to $C_6$ alkoxy, $C_1$ to $C_6$ haloalkoxy, $C_1$ to $C_6$ alkylthio, $C_1$ to $C_6$ alkylsulfinyl, $C_1$ to $C_6$ alkylsulfonyl, $C_1$ to $C_6$ haloalkylsulfinyl, $C_1$ to $C_6$ haloalkylsulfonyl, sulfo, $C_1$ to $C_6$ alkoxysulfonyl, sulfamoyl, N-($C_1$ to $C_6$ alkyl) sulfamoyl, N,N-Di($C_1$ to $C_6$ alkyl)sulfamoyl, carboxy, ($C_1$ to $C_6$ alkoxy)carbonyl, carbamoyl, N-($C_1$ to $C_6$ alkyl)carbamoyl, N,N-

(di($C_1$ to $C_6$ alkyl)carbamoyl, phenyl, phenoxy, phenylthio, and the groups substituted phenyl, substituted phenoxy and substituted phenylthio wherein in each group the phenyl ring is substituted with one to three substituents chosen from the group consisting of halogen, $C_1$ to $C_6$ alkyl, $C_1$ to $C_6$ haloalkyl, $C_1$ to $C_6$ alkoxy, nitro and cyano;

$R^1$ is chosen from the group consisting of hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl, and $C_2$ to $C_6$ alkoxycarbonyl;

$R^2$ is chosen from the group consisting of hydrogen, $C_1$ to $C_6$ alkyl, $C_2$ to $C_6$ alkenyl, $C_2$ to $C_6$ alkoxyalkyl and $C_1$ to $C_6$ haloalkyl, or $R^1$ and $R^2$ together may form a methylene, ethylidene, propylidene or isopropylidene group;

W is chosen from the group consisting of cyano, thiocarbamoyl,

and $CH_2Z$ wherein:

G is chosen from the group consisting of hydroxy, mercapto, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, $C_3$ to $C_7$ cycloalkoxy, $C_3$ to $C_7$ cycloalkoxy substituted with one or two $C_1$ to $C_4$ alkyl groups, phenoxy, phenylthio, benzyloxy, benzylthio, the group $C_1$ to $C_{10}$ alkoxy substituted with a substituent chosen from the group consisting of $C_1$ to $C_6$ alkoxy, amino, ammonio, cyano, N-($C_1$ to $C_6$ alkyl)amino, N,N-di($C_1$ to $C_6$ alkyl)amino, and N,N,N-tri($C_1$ to $C_6$ alkyl)ammonio, the groups phenoxy, phenylthio, benzyloxy and benzylthio wherein in each group the phenyl ring is substituted with from one to three substituents chosen from the group consisting of halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group $—NHSO_2R^3$ wherein $R^3$ is chosen from $C_1$ to $C_{10}$ alkyl and $C_1$ to $C_{10}$ haloalkyl, the group $—NR^4R^5$ wherein $R^4$ and $R^5$ are independently chosen from the group consisting of hydrogen, $C_1$ to $C_6$ alkyl, phenyl and benzyl and the group $—O—N=R^6$ wherein $R^6$ is a $C_1$ to $C_{10}$ alkylidene group;

and Z is chosen from halogen, hydroxy, mercapto, $C_1$ to $C_{10}$ alkoxy, $C_1$ to $C_{10}$ haloalkoxy, $C_1$ to $C_{10}$ alkylthio and the group $NR^4R^5$ wherein $R^4$ and $R^5$ are as hereinbefore defined;

X and Y are independently chosen from oxygen and sulfur;

k, l and m are independently chosen from 0 and 1 provided that k+l+m is 0, 1 or 2; and n is 0, 1 or 2.

2. A compound according to claim 1 wherein:

A, B, D, E, U and V are independently chosen from the group consisting of hydrogen, halogen, nitro, cyano, thiocyano, amino, $C_1$ to $C_6$ alkylamino, di($C_1$ to $C_6$ alkyl)amino, $C_1$ to $C_6$ alkyl, $C_1$ to $C_6$ haloalkyl, $C_2$ to $C_6$ alkenyl, $C_3$ to $C_7$ cycloalkyl, $C_1$ to $C_6$ alkoxy, $C_1$ to $C_6$ alkylthio, $C_1$ to $C_6$ alkylsulfinyl, $C_1$ to $C_6$ alkylsulfonyl, ($C_1$ to $C_6$ alkoxy)carbonyl, phenyl, phenoxy, phenylthio, and the groups substituted phenyl, substituted phenoxy and substituted phenylthio wherein in each group the phenyl ring is substituted with from one to three substituents chosen from the group consisting of halogen, $C_1$ to $C_6$ alkyl, $C_1$ to $C_6$ haloalkyl, $C_1$ to $C_6$ alkoxy, nitro and cyano, $R^1$ is chosen from the group consisting of hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl and ($C_1$ to $C_6$ alkoxy)carbonyl;

$R^2$ is chosen from the group consisting of hydrogen, $C_1$ to $C_6$ alkyl, $C_2$ to $C_6$ alkenyl, $C_2$ to $C_6$ alkoxyalkyl, and $C_1$ to $C_6$ haloalkyl or $R^1$ and $R^2$ together form a methylene, ethylidene, propylidene or isopropylidene group;

W is chosen from the group consisting of cyano; thiocarbamoyl,

and $—CH_2Z$ wherein:

G is chosen from the group consisting of hydroxy, mercapto, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_3$ to $C_7$ cycloalkoxy, $C_3$ to $C_7$ cycloalkoxy substituted with one or two $C_1$ to $C_4$ alkyl groups, phenoxy, phenylthio, benzyloxy, benzylthio, the group $C_1$ to $C_{10}$ alkoxy substituted with an hydroxy or a $C_1$ to $C_6$ alkoxy group, the groups phenoxy, phenylthio, benzyloxy and benzylthio wherein in each group the phenyl ring is substituted with one or two substituents chosen from the group consisting of halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group $—NHSO_2R^3$ wherein $R^3$ is chosen from $C_1$ to $C_{10}$ alkyl and $C_1$ to $C_{10}$ haloalkyl, and the group $—NR^4R^5$ wherein $R^4$ and $R^5$ are independently chosen from the group consisting of hydrogen, $C_1$ to $C_6$ alkyl, $C_1$ to $C_6$ haloalkyl, $C_1$ to $C_6$ hydroxyalkyl, phenyl and benzyl; and Z is chosen from halogen, hydroxy, mercapto, $C_1$ to $C_{10}$ alkoxy, $C_1$ to $C_{10}$ haloalkoxy, $C_1$ to $C_{10}$ alkylthio and the group $NR^4R^5$ wherein $R^4$ and $R^5$ are independently chosen from the group consisting of hydrogen, $C_1$ to $C_6$ alkyl, $C_1$ to $C_6$ haloalkyl, $C_1$ to $C_6$ hydroxyalkyl, phenyl and benzyl;

X and Y are independently chosen from oxygen and sulfur;

k, l and m are independently chosen from 0 and 1 provided that k+l+m is 0 or 1; and n is 0, 1 or 2.

3. A compound according to claim 1 wherein:

A, B, D and E are independently chosen from the group consisting of hydrogen, halogen, nitro, cyano, amino, $C_1$ to $C_6$ alkylamino, di($C_1$ to $C_6$ alkyl)amino, $C_1$ to $C_6$ alkyl, $C_1$ to $C_6$ haloalkyl, $C_2$ to $C_6$ alkenyl, $C_1$ to $C_6$ alkoxy, $C_1$ to $C_6$ haloalkoxy, $C_1$ to $C_6$ alkylthio, carboxy and ($C_1$ to $C_6$ alkoxy)carbonyl;

U and V are independently chosen from the group consisting of hydrogen, halogen, nitro, cyano, $C_1$ to $C_6$ alkyl and $C_1$ to $C_6$ haloalkyl;

$R^1$ is chosen from the group consisting of hydrogen, $C_1$ to $C_6$ alkyl, $C_2$ to $C_6$ alkoxyalkyl and ($C_1$ to $C_6$ alkoxy)carbonyl;

$R^2$ is chosen from hydrogen and $C_1$ to $C_6$ alkyl;
W is chosen from the group

and —$CH_2Z$ wherein:

G is chosen from the group consisting of hydroxy, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, cyclohexyloxy, phenoxy, benzyloxy, the group $C_1$ to $C_{10}$ alkoxy substituted with a substituent chosen from the group consisting of $C_1$ to $C_6$ alkoxy, amino, N—($C_1$ to $C_6$ alkyl)amino, N,N-di($C_1$ to $C_6$ alkyl)amino and N,N,N-tri($C_1$ to $C_6$ alkyl)ammonio, the group —$NR^4R^5$ wherein $R^4$ and $R^5$ are independently chosen from hydrogen, $C_1$ to $C_6$ alkyl, $C_1$ to $C_6$ hydroxyalkyl, $C_1$ to $C_6$ haloalkyl and phenyl, the group OM wherein M is an alkali metal ion, alkaline earth metal ion or an ammonium ion $HN^{\oplus}R^7R^8R^9$ wherein $R^7$, $R^8$ and $R^9$ are independently chosen from the group consisting of hydrogen, $C_1$ to $C_6$ alkyl, $C_1$ to $C_6$ hydroxyalkyl, phenyl and benzyl, the group —$NHSO_2R^3$ wherein $R^3$ is $C_1$ to $C_6$ alkyl, and the group —O—N=$R^6$ wherein $R^6$ is a $C_1$ to $C_{10}$ alkylidene group; and Z is chosen from the group consisting of halogen, hydroxy, mercapto, $C_1$ to $C_{10}$ alkoxy, and the group —$NR^4R^5$ wherein $R^4$ and $R^5$ are independently chosen from the group consisting of hydrogen, $C_1$ to $C_6$ alkyl, $C_1$ to $C_6$ hydroxyalkyl, $C_1$ to $C_6$ haloalkyl and phenyl;

X and Y are both oxygen;
m is 0 and k and l are independently chosen from 0 and 1 provided that k+l is 0 or 1; and
n is 0 or 2.

4. A compound according to claim 3 wherein:
A, B, D and E are independently chosen from the group consisting of hydrogen, halogen, $C_1$ to $C_6$ alkyl and $C_1$ to $C_6$ haloalkyl;
U and V are independently chosen from hydrogen and halogen;
$R^1$ and $R^2$ are independently chosen from hydrogen and $C_1$ to $C_6$ alkyl;
W is the group

wherein G is chosen from hydroxy, $C_1$ to $C_{10}$ alkoxy, $C_2$ to $C_{10}$ alkenyloxy, $C_2$ to $C_{10}$ alkynyloxy, $C_3$ to $C_7$ cycloalkoxy and the group OM wherein M is an alkaline metal ion or an alkaline earth metal ion;
X and Y are both oxygen;
k is chosen from 0 and 1; and
l, m and n are each 0.

5. A compound according to claim 4 of formula II

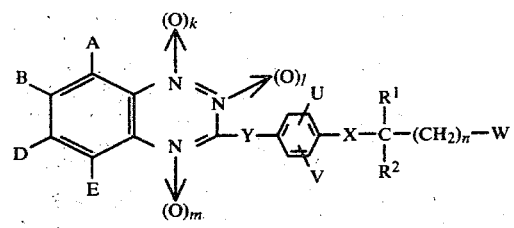

6. A compound according to claim 5 inclusive wherein:
A, D, E and V are hydrogen;
B is chosen from hydrogen, halogen, $C_1$ to $C_6$ alkyl and $C_1$ to $C_6$ haloalkyl;
U is chosen from hydrogen and halogen;
$R^1$ an $R^2$ are chosen from hydrogen and $C_1$ to $C_6$ alkyl;
W is the group

wherein G is chosen from the group consisting of hydroxy, $C_1$ to $C_6$ alkoxy, cyclohexyloxy and the group OM wherein M is an alkali metal ion;
X and Y are both oxygen;
k is 0 or 1; and l, m and n are each 0.

7. A compound according to claim 6 wherein:
A, D, E, U, V and $R^2$ are hydrogen;
B is chosen from hydrogen, halogen, methyl, ethyl and trifluoromethyl;
$R^1$ is methyl;
W is the group

wherein G is chosen from $C_1$ to $C_6$ alkoxy and cyclohexyoxy;
X and Y are both oxygen;
k is 0 or 1; and
l, m and n are each 0.

8. A compound according to claim 7 chosen from the group consisting of the methyl, ethyl, n-propyl, isopropyl, n-butyl, isobutyl, secondary butyl and cyclohexyl esters of 2-{4-[(7-chloro-1-oxide-1,2,4-benzotriazin-3-yl)oxy]phenoxy}propionate, 2-{4-[7-fluoro-1-oxide-1,2,4-benzotriazin-3-yl)oxy]-phenoxy}propionate and 2-{4-[(1-oxide-1,2,4-benzotriazin-3-yl)oxy]phenoxy}-propionate.

9. A compound of formula VIII

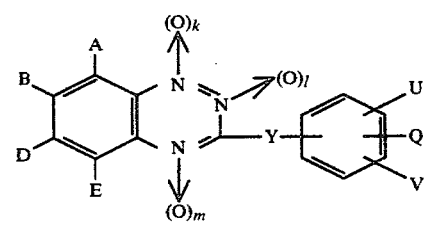

wherein A, B, D, E, Y, U, V, k, l and m are as defined according to claim 1 and Q is chosen from hydroxy, mercapto, $C_1$ to $C_6$ alkoxy and $C_1$ to $C_6$ alkylthio.

10. A herbicidal composition comprising as active ingredient a compound as defined according to claim 1 and a carrier therefor.

11. A process for severely damaging or killing unwanted plants which process comprises applying to said plants, or to the growth medium of said plants, an effective amount of a compound as defined according to claim 1.

12. A process for selectively controlling the growth of monocotyledonous weeds in dicotyledonous crops which process comprises applying to said crop, or to the growth medium of said crop, a compound as defined according to claim 1 in an amount sufficient to severely damage or kill the weeds but insufficient to substantially damage the crop.

13. A process according to claim 11 wherein the compound is applied at a rate in the range from 0.005 to 20 kilograms per hectare.

* * * * *